United States Patent
Deslauriers

[19]
[11] Patent Number: 6,120,288
[45] Date of Patent: Sep. 19, 2000

[54] DEVICE AND METHOD FOR MANDIBULAR FIXATION

[76] Inventor: Richard J. Deslauriers, 78 Joseph St., Waterbury, Conn. 06705

[21] Appl. No.: 09/159,638

[22] Filed: Sep. 24, 1998

Related U.S. Application Data

[60] Provisional application No. 60/059,987, Sep. 25, 1997.

[51] Int. Cl.$^7$ ...................................................... A61C 3/00
[52] U.S. Cl. .................................... 433/9; 433/23; 433/39
[58] Field of Search ........................... 606/74, 151; 433/9, 433/23, 39; 602/7

[56] References Cited

U.S. PATENT DOCUMENTS

| | | |
|---|---|---|
| 3,874,876 | 4/1975 | Dart et al. |
| 3,881,473 | 5/1975 | Corvi et al. |
| 4,889,485 | 12/1989 | Iida ............................................. 433/9 |
| 4,904,188 | 2/1990 | Baurmash . |
| 5,102,332 | 4/1992 | Uthoff . |
| 5,110,290 | 5/1992 | Wong .......................................... 433/9 |
| 5,480,301 | 1/1996 | Farzin-Nia et al. ......................... 433/9 |

FOREIGN PATENT DOCUMENTS

2684539  12/1991  France .

OTHER PUBLICATIONS

International Search Report dated Jan. 28, 1999.

*Primary Examiner*—Michael Buiz
*Assistant Examiner*—Julian W. Woo
*Attorney, Agent, or Firm*—Baker Botts L.L.P.

[57] ABSTRACT

A device and method for mandibular fixation are disclosed. The bondable bracket brace includes a cloth-like body having a first surface for attachment to a tooth surface and a plurality of attachment points on the cloth-like body. The cloth like body may be made of Kevlar®, nylon, fine metal mesh, or combinations thereof The bondable bracket brace may also include lift points for removing the bondable bracket brace, and may also include fiber straps for securing the bondable bracket brace to a tooth surface. A method of mandibular fixation includes the steps of: (1) preparing a surface of the teeth, (2) applying a first adhesive layer to the prepared surface; (3) positioning a bondable bracket brace with a cloth-like body on the first adhesive layer, (4) curing the adhesive; and (5) securing an object to the bondable bracket brace with a linking member. A system of mandibular fixation includes a first bondable bracket brace having a plurality of attachment points for attachment to a tooth surface, a bondable bracket brace having a plurality of attachment points for attachment to a tooth surface, and linking members for securing the attachment points on the first bondable bracket brace to the attachment points on the second bondable bracket brace. A bone immobilization system is also disclosed and includes a flexible cloth-like body for surrounding a bone to be immobilized and a curable adhesive applied to the cloth-like body. When the curable adhesive is cured the cloth-like body becomes rigid, immobilizing the bone.

29 Claims, 12 Drawing Sheets

DEVICE AND METHOD FOR MANDIBULAR FIXATION

This appln. claim the benefit of U.S. Provisional No. 60/059,987 filed Sep. 25, 1997.

BACKGROUND OF THE INVENTION

1. Field of the Invention

The invention relates generally to a device and method for mandibular fixation. More particularly, the present invention relates to a two-state, high-surface contact area, rapid-cure, bondable-support bracket brace and fiber strap and a method for its use.

2. Description of Related Art

The current art of managing maxillomandibular fractures is based on securing an arch bar to immobilize fracture segments. Known arch bars are designed to provide stabilization of fractures of the maxilla, the mandible, or both. The original arch bar was an ordinary round bar, eventually modified to include a bar, flattened on one side.

For over a decade, bonded arch bars have been used in maxillomandibular trauma, reconstruction, and various other oral surgical procedures. The prefabricated, one-piece, metal, mesh-backed arch bar for direct bonding is commercially available. The device is malleable enough to be contoured to the buccal tooth surface yet firm enough to withstand the forces that tend to displace it. Other than the addition of a metal mesh backing, these direct bonding arch bars are similar to the modified arch bar.

Bonded arch bars of this design have had limited success. The metal mesh increased surface contact marginally. In addition to low-holding forces, the sharp metal mesh was dangerous and required multiple epoxy applications, numerous tools, and considerable skill to apply.

Through the years, many different methods of fixing arch bars have been developed. The most popular method of fixing arch bars is via interdental wires. Plastic cable ties, disclosed in U.S. Pat. No. 5,613,853 to Chasan et al, bone screws and direct bonding have also been used with limited success.

Periodental injury is always a threat with interdental wires or cables because the wires must be placed below the gingival margins to guarantee stability. With the inherent difficulty of maintaining proper oral hygiene and the necessity to penetrate the interdental papilla with the large profile circumdental wire or strap, gingival inflammation and damage are expected. Any implants are also expected to suffer damage. Moreover, the use of interdental wires typically results in gum bleeding, which increases the likelihood of the transmission of diseases, such as hepatitis and HIV, to the surgeon. Additionally, the open wounds caused by the interdental wires increase the possibility of infection to the patient.

Bone screws in the maxilla and mandible, linked by a loop of wire, have also been described. This method, however, is not applicable to all fractures, although it does reduce the risk of skin puncture associated with passing interdental wires.

SUMMARY OF THE INVENTION

Accordingly, a need has arisen for a device and method of mandibular fixation that overcomes these and other drawbacks associated with the related art.

According to an embodiment of the present invention, a bondable bracket brace is disclosed. The bondable bracket brace includes a cloth-like body having a first surface for attachment to a tooth surface and a plurality of attachment points on the cloth-like body. The cloth like body may be made of Kevlar®, nylon, fine metal mesh, or combinations thereof. The bondable bracket brace may also include lift points for removing the bondable bracket brace, and may also include fiber straps for securing the bondable bracket brace to a tooth surface.

According to another embodiment of the present invention, a method for mandibular fixation is disclosed. A method of mandibular fixation includes the steps of: (1) preparing a surface of the teeth, (2) applying a first adhesive layer to the prepared surface; (3) positioning a bondable bracket brace with a cloth-like body on the first adhesive layer, (4) curing the adhesive; and (5) securing an object to the bondable bracket brace with a linking member.

According to another embodiment of the present invention, a system of mandibular fixation is disclosed. The system of mandibular fixation includes a first bondable bracket brace having a plurality of attachment points for attachment to a tooth surface, a second bondable bracket brace having a plurality of attachment points for attachment to a tooth surface, and linking members for securing the attachment points on the first bondable bracket brace to the attachment points on the second bondable bracket brace.

According to another embodiment of the invention, a bone immobilization device is disclosed. The bone immobilization device includes a flexible cloth-like body for surrounding a bone to be immobilized and a curable adhesive applied to the cloth-like body. When the curable adhesive is cured the cloth-like body becomes rigid, immobilizing the bone. The cloth-like body may be made of Kevlar®, nylon, fine metal mesh, or combinations thereof. The cloth-like body may be pre-impregnated with the curable adhesive.

According to another embodiment of the invention, a method for bone immobilization includes the steps of: (1) preparing an area for immobilization; (2) applying a cloth-like body to the prepared area for immobilization; (3) applying a curable adhesive to the cloth-like body; and (4) curing the curable adhesive. The step of preparing an area for immobilization may include setting a bone. The cloth-like body may be pre-impregnated with a curable adhesive. Curing the adhesive may include exposing the curable adhesive to energy, such as visible light, ultraviolet light, or electromagnetic energy.

The device and method according to the present invention provide the technical advantage of stabilizing the mandible and/or the maxilla while minimizing periodental trauma. The device and method of the present invention provide the additional technical advantage of maximizing contact area with tooth surfaces, resulting in a stronger bond between the device and tooth surface. It is another technical advantage that it provides a fast, fifteen minute application process. Another technical advantage is that due to the bloodless application, there is a decreased risk of the transmission of disease from the patient to the surgeon, or vice-versa. It is another technical advantage that a bone immobilizing device that has a rapid cure time is disclosed.

BRIEF DESCRIPTION OF THE DRAWINGS

FIG. 1b depicts a side view of a bondable bracket brace shown in FIG. 1a.

FIG. 2b depicts a section view of the bondable bracket shown in FIG. 2a.

DETAILED DESCRIPTION OF PREFERRED EMBODIMENTS

The preferred embodiment of the present invention and its advantages are best understood by referring to FIGS. 1 through 7 of the drawings, like numerals being used for like and corresponding parts of the various drawings.

The present invention provides a bondable bracket brace with a cloth-like body that is useful in the fixation of fractures of the mandible and/or maxilla. A bondable bracket brace can be adhered to the surface of the upper teeth and the lower teeth, and subsequently hardened. The bondable bracket brace incudes a number of attachment points enabling one device to be secured to another. In a preferred embodiment, a mandibular fixation device includes two bondable bracket braces that are adhered to the surfaces of the upper and lower teeth respectively. The two bondable bracket braces may be secured together, for instance, by using wire, to tie together the attachment points on the upper and lower bondable bracket braces. Use of these bondable bracket braces enables one to avoid the use of interdental wires and the resulting periodental trauma.

Figure 1A:
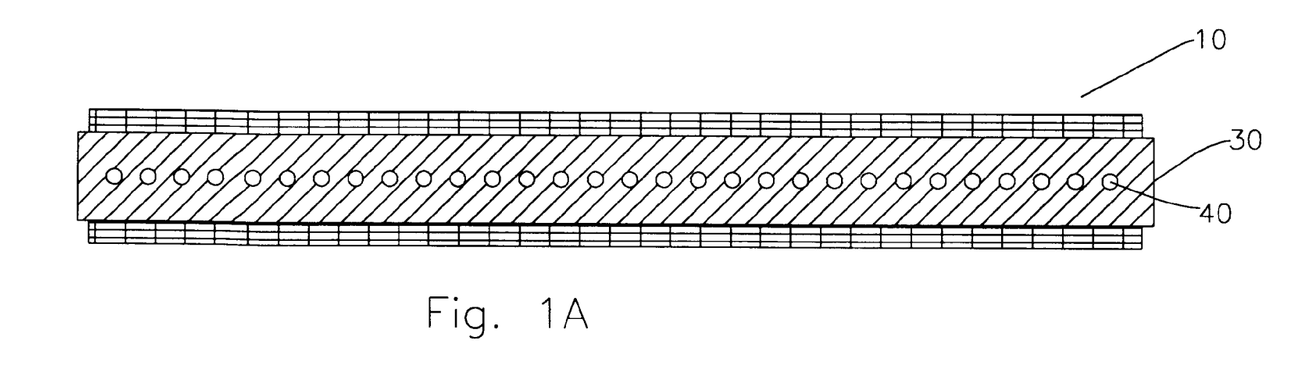
FIG. 1a depicts a front view of a bondable bracket brace according to an embodiment of the present invention.
Figure 1B:
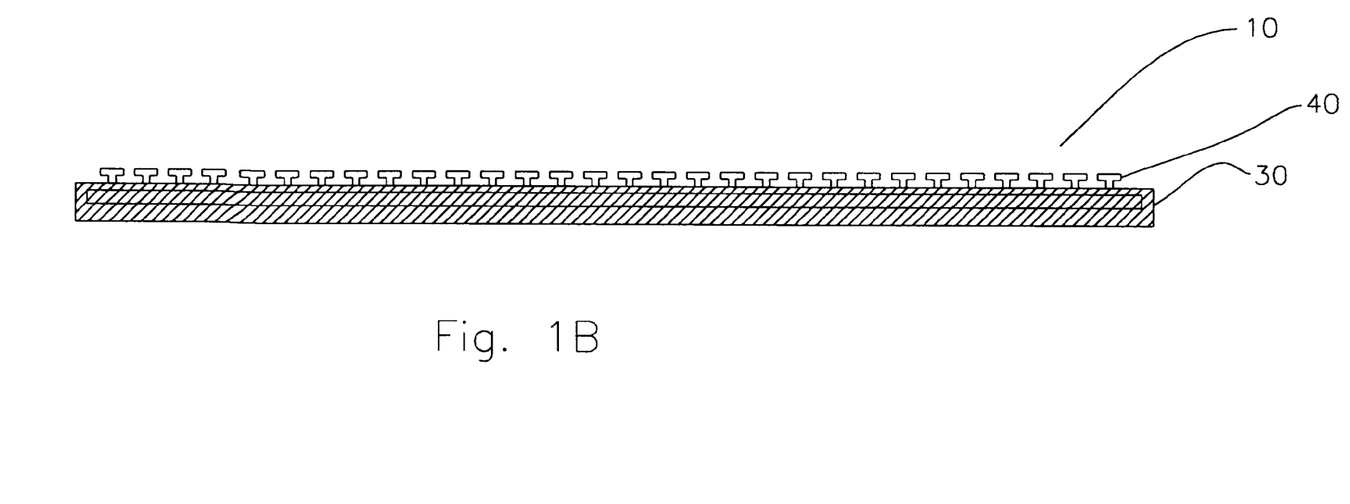

FIGS. 1a and 1b depict front and side views, respectively, of one embodiment of a bondable bracket brace 10. Bondable bracket brace 10 includes a cloth-like body 30 having a plurality of attachment points 40.

Cloth-like body 30 may be constructed of an extremely strong, light, shapeable, and moldable cloth-like material. Suitable materials for cloth-like body 30 include nylon, and a combination of Kevlar®, manufactured by DuPont Corporation, and a fine metal mesh or similar material. A combination of nylon and Kevlar® may also be used. The invention, however, is not limited to the use of nylon or a Kevlar®-based material. Any other suitable materials or combinations may also be used.

Cloth-like body 30 exists in two distinct states. In the first state, cloth-like body 30 is malleable, shapeable, and moldable. In the second state, however, cloth-like body hardens, having properties consistent with a rigid fiber reinforced medical grade Class VI plastic arch bar. There is a rapid transition from the first state to the second state, limited only by the time it takes for the adhesive to cure.

Fine fibers emanate from cloth-like body 30 and may operate to fill small voids and gaps between the tooth surface and cloth-like body 30, in order to maximize bond surface contact and strength. Cloth-like body 30 can conform to or cover irregular shapes and configurations with minimal manipulation. By maximizing the surface contact area between the tooth and bondable bracket brace 10, chemical bonding forces may be optimized.

When an adhesive, such as an epoxy, is used, the epoxy and fine fibers fill or migrate to the interdental space (the space between adjacent teeth) in order to increase the surface contact area and thereby provide maximum mechanical bonding. Cloth-like body 30 captures the appropriate amount of epoxy. In one embodiment, cloth-like body 30 captures epoxy until it is saturated. This capturing quality provides for consistent, repeatable bonds from surgeon to surgeon. It also minimizes adhesive overflow onto the patient. The resulting cloth, cloth fibers, cloth and epoxy, and cloth fibers and epoxy, cover and fill the interdental space. Epoxy in the interdental space provides for a mechanical wedge because the cured epoxy cannot be pulled out from the interdental space, while the epoxy and cloth that is adjacent to the tooth provides for a direct chemical bond with the tooth surface.

In one embodiment, the adhesive adheres to cloth-like body 30 in such a manner that upon removal, the adhesive and cloth-like body 30 of bondable bracket brace 10 are removed as one unit. This may be caused by a stronger chemical bond between the adhesive and cloth-like body of bondable brace 10 than between the adhesive and the tooth surface.

In another embodiment of the present invention, cloth-like body 30 may be pre-impregnated with an adhesive and provided in protective packaging. This results in a more rapid, and potentially less messy, application of bondable bracket brace 10 to the tooth surface. With experience, it is possible for the application of the bondable bracket brace to take less than fifteen minutes.

Attachment points 40 may be used to secure one bondable bracket brace 10 to another bondable bracket brace 10, or to other equipment. Attachment points 40 may be made of a strong, non-corrosive material, such as stainless steel; other suitable materials, however, may also be used. Attachment points 40 may have various shapes and orientations and are preferably configured to minimize the risk of trauma to the inside of the mouth. In the embodiment shown in FIGS. 1a–1c, attachment points 40 have a pin and head construction. In another embodiment, eyelets may be used as attachment points 40. In yet another embodiment, hooks may be used as attachment points 40.

A linking member, such as standard surgical wire, elastics, wire ties, or any other suitable linking member, may be used to secure attachment points of one bondable bracket brace 10 to another bondable bracket brace 10. In one embodiment, fibers may be used as linking members. Wire tie locks, general interlocks, internal structures, general fasteners, quick fasteners, one piece arches, or any suitable anchoring means may be used.

Figure 1C:
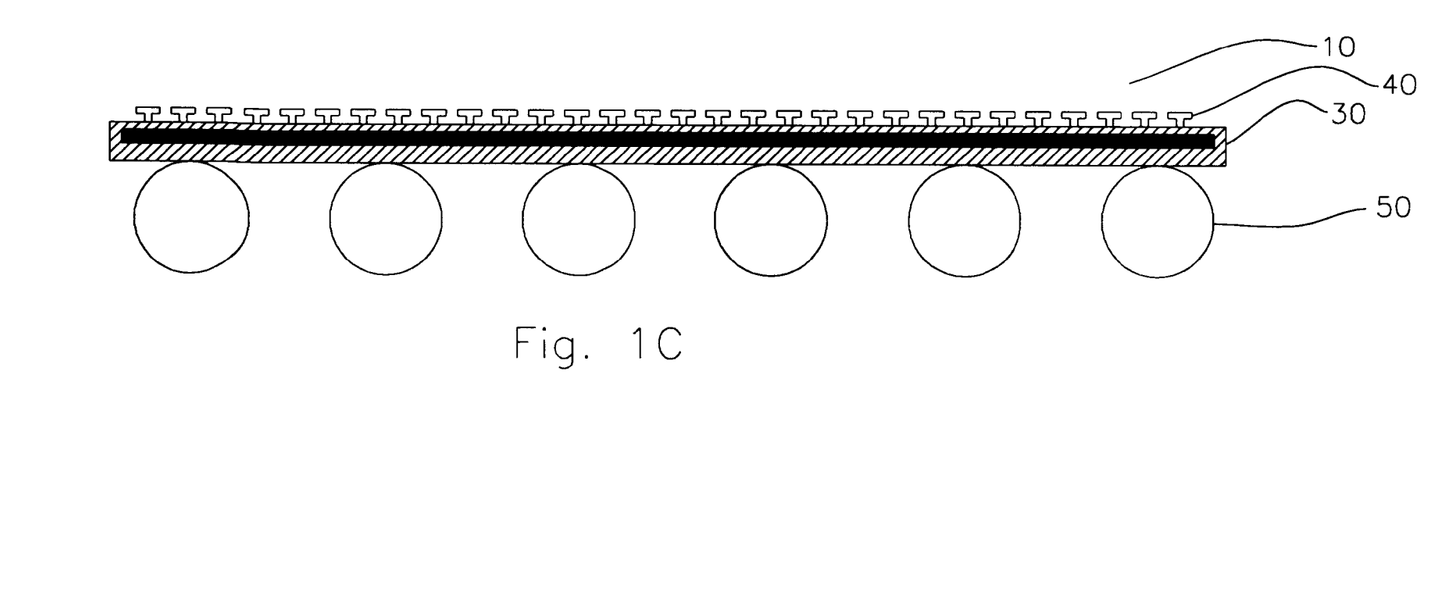
FIG. 1c depicts a side view of a bondable bracket brace including fiber straps according to another embodiment of the present invention.

Referring to FIG. 1c, in another embodiment, bondable bracket brace 10 may also include a plurality of fiber straps 50. Fiber straps 50 may be used to secure objects, such as the bondable bracket brace 10. This may be used where minimal surface area for epoxy bonding between attachment points 40 exists. For example, fiber straps 50 can slip into very small clefts. Fiber straps 50 are inherently strong, flexible and stretch minimally under tension. Suitable materials for fiber straps 50 include nylon strands, Kevlar® strands, and any other suitable material. In one embodiment, nylon strands are used.

Fiber straps 50 act much like standard interdental wires, yet they produce minimal trauma during insertion. Fiber straps 50, like dental floss, may be coated with wax or any other suitable lubricant, and may be manipulated into very small clefts with ease. In one embodiment, fiber straps 50 may be constructed from fibers, which are flexible, stretch less than standard interdental wires, and may be passed individually and reconstructed into one large fiber.

Figure 2A:
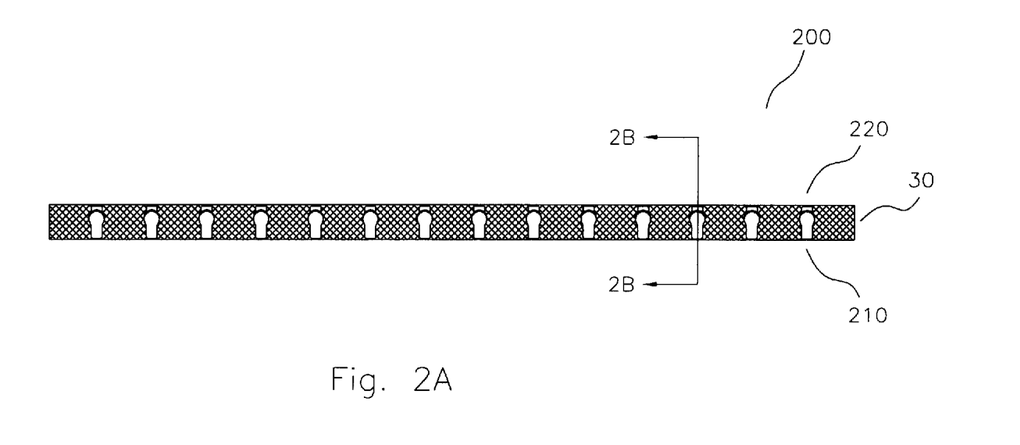
FIG. 2a depicts a front view of a bondable bracket having an improved metal tab configuration according to another embodiment of the present invention.
Figure 2B:
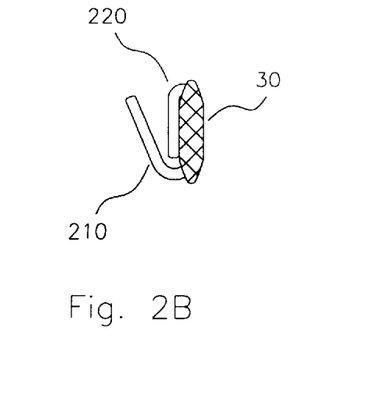

Referring to FIGS. 2a and 2b, another embodiment of a bondable bracket brace is shown. In FIG. 2a, bondable bracket brace 200 includes cloth-like body 30, attachment points 210, and lift tabs 220. Attachment points 210 may be made of a non-corrosive material, such as stainless steel. Other suitable materials may also be used.

Attachment points 210 may have a variety of shapes and orientations. In the embodiment shown in FIGS. 2a and 2b, attachment points 210 are located at about one of the sides of cloth-like body 30 and have a hook-like shape. Thus, when two bondable bracket braces 200 are provided opposite each other, attachment points 210 will be located closely to each other, to the point of being or almost being in contact with each other. In another embodiment, attachment points 210 may have a pin and head construction such as is shown in FIG. 1.

Bondable bracket brace 220 also includes lift tabs 220 to assist in the removal of bondable bracket brace 200 from the tooth surface. Specifically, lift tabs 220 are preferably fabricated of a non-stick material and are interwoven into cloth-like body 30. Thus, lift tabs 220 prevent bondable bracket brace 220 from adhering to the tooth surface. In one embodiment, lift tabs 220 are made of Teflon®, manufactured by DuPont Corporation. Other materials having the same characteristics may also be used.

In one embodiment, each attachment point 210 has a corresponding lift tab 220. This corresponding lift tab 220 may be positioned directly across from attachment point 210. In other embodiments, more or fewer lift tabs 220 may be provided. In general, bondable bracket brace 200 is provided with a number of lift tabs 220 sufficient to enable bondable bracket brace 200 to be removed without inducing trauma to the mandible the maxilla or both. Bondable bracket brace 200 may also be provided with lift tabs 220 to ease removal.

Bondable bracket brace 200 may be pre-impregnated with an adhesive, and packaged and shipped in such a manner as to prevent bondable bracket brace 200 from changing from a malleable state to a firm state. In one embodiment, bondable bracket brace 200 is shipped in a pre-assembled and pre-impregnated state where it is completely prepared for application to the tooth surface, saving time and discomfort in application.

Bondable bracket braces 10 and 200 may come in a variety of sizes in order to conform to the size of an individual's mouth. Further, if bondable bracket brace 10 or 200 is too long for the tooth surface, it can be shortened with appropriate dental tools to customize the fit to the individual's mouth.

Figure 3:
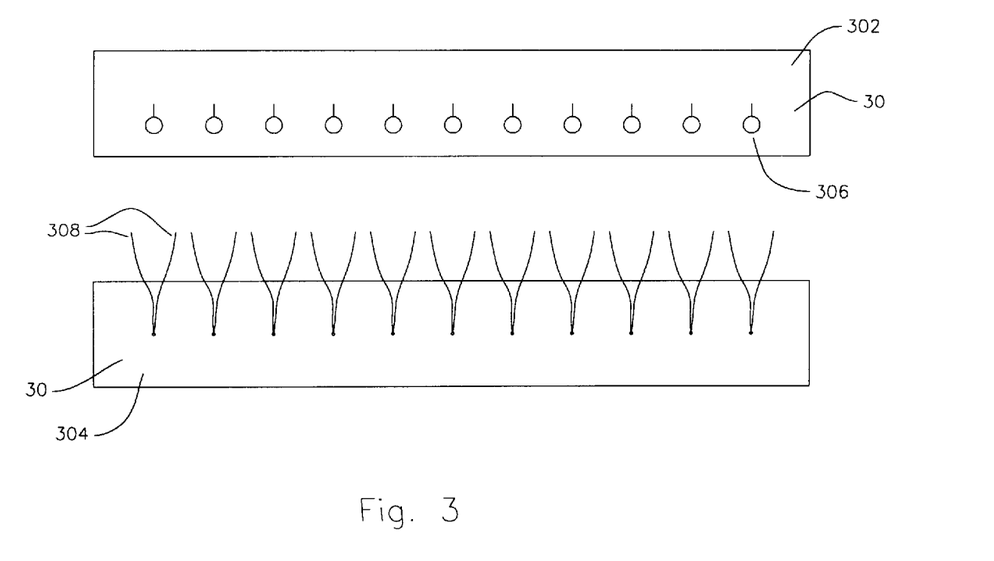
FIG. 3 depicts a mandibular fixation device comprising male and female bondable bracket braces according to another embodiment of the invention.

Referring to FIG. 3, in another embodiment, a pair of bondable bracket braces 302 and 304 may be provided. In this embodiment, female bondable bracket brace 302 has attachment points 306, which may be small eyelets, studs, or similar devices. Male bondable bracket brace 304 has fiber or elastic straps 308 for securing to attachment points 306. In one embodiment, once male bondable bracket brace 304 and female bondable bracket brace 302 are attached and cured, straps 308 are secured to attachment points and tied, with the excess straps 308 being removed. In another embodiment, straps 308 comprise elastic loops that are looped around attachment points 306. Since bondable bracket braces 302 and 304 are provided with attachment points and straps respectively, no further linking members are required to secure bondable bracket braces 302 and 304 together. Thus, the number of pieces and the application time are correspondingly reduced.

Figure 4:
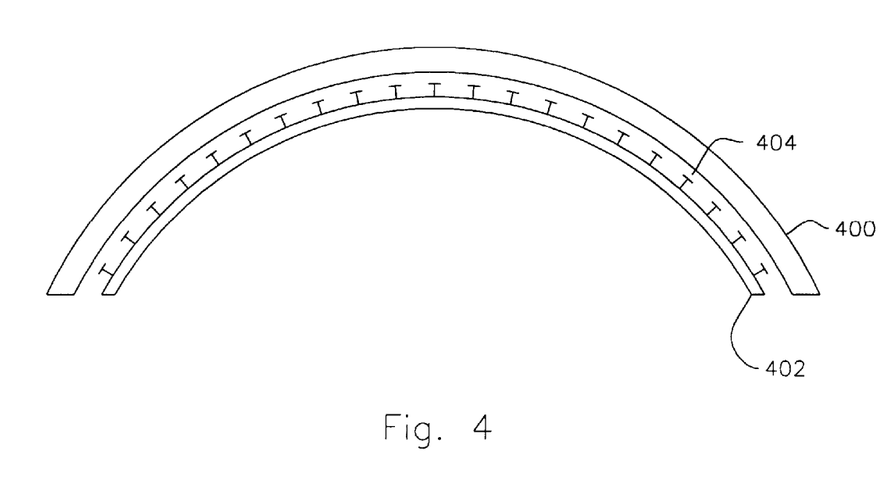
FIG. 4 depicts a holding bracket for holding and positioning a bondable bracket brace according to another embodiment of the invention.

Referring to FIG. 4, a holding bracket 400 may be used to assist in the holding and positioning of any bondable bracket brace. Specifically, holding bracket 400 enables a surgeon to position bondable bracket brace 402 without contacting bondable bracket brace 402 or the prepared tooth surface. Moreover, in the case of bondable bracket brace 402 being impregnated with adhesive, holding bracket 400 enables a surgeon to position bondable bracket brace 402 without the adhesive contacting the surgical gloves of the surgeon. Holding bracket 400 may be made of Teflon®, or it may be a metal or plastic covered with Teflon® or some other material that will not adhere to bondable bracket brace 402. Holding bracket 400 may be curved or it may be straight. Further, holding bracket 400 may be flexible, or it may be stiff.

Holding bracket 400 may be provided with a receiving slot (not shown) for receiving attachment points 404. In another embodiment, a plurality of receiving holes (not shown) may be provided for receiving attachment points 404. Attachment points 404 may "click" into receiving slot (not shown) or receiving holes (not shown) and may thereby temporarily secure bondable bracket brace 402 to holding bracket 400.

Bondable bracket brace 402 may be positioned by hand through holding bracket 400. Once bondable bracket brace 402 is positioned, holding bracket 400 is removed and bondable bracket brace 402 is cured in position.

Figure 5:
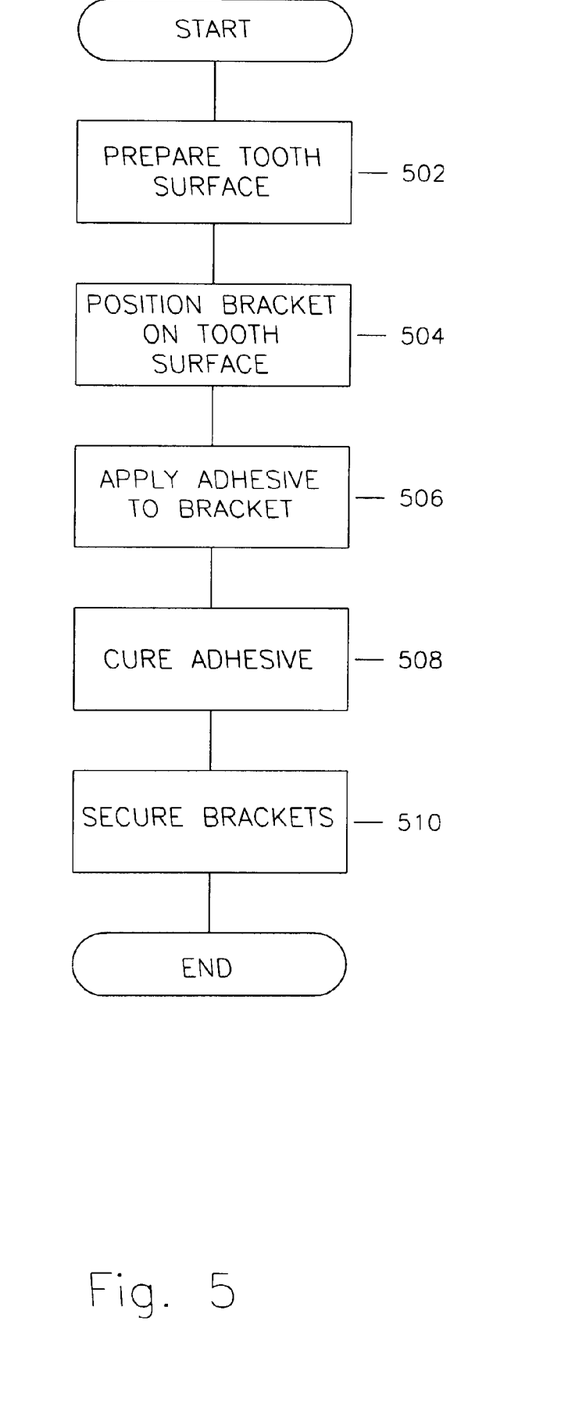
FIG. 5 depicts a flowchart of a method of mandibular fixation according to one embodiment of the invention.

Referring to FIG. 5, a method of mandibular fixation according to one embodiment of the present invention will now be explained in conjunction with the bondable bracket brace 200 of FIGS. 2a and 2b. This process may also be used to apply bondable bracket brace 10 of FIGS. 1a–c, 3, 4, or any other embodiment of the bondable bracket brace.

In step 502, the tooth surface is prepared. To do this, the patient's oral cavity is exposed and the tooth surface is prepared, as per standard dental procedures. An acid gel is then applied to the tooth surface for several seconds in order to etch the dentin layer of the tooth and remove the smear layer, thereby exposing the collagen fiber matrix. A 37% phosphoric acid gel or similar acid gel is suitable and is known in the art. The acid also slightly opens the dentinal tubules to optimize epoxy bonding. The acid gel is then removed, and the exposed surface is dried.

Figure 6A:
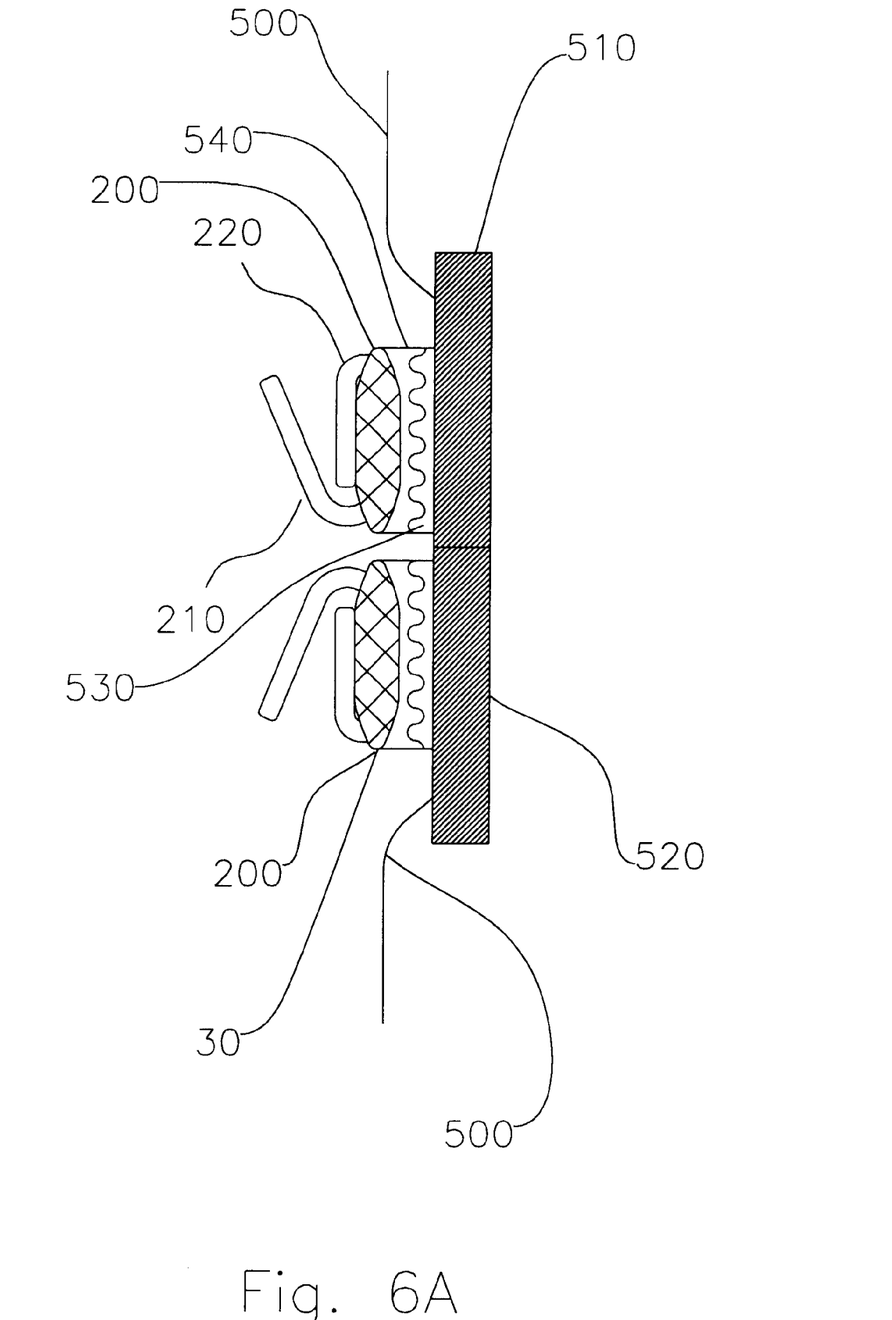
FIG. 6a depicts a schematic side view of two bondable bracket braces positioned on a tooth surface according to one embodiment of the present invention.
Figure 6B:
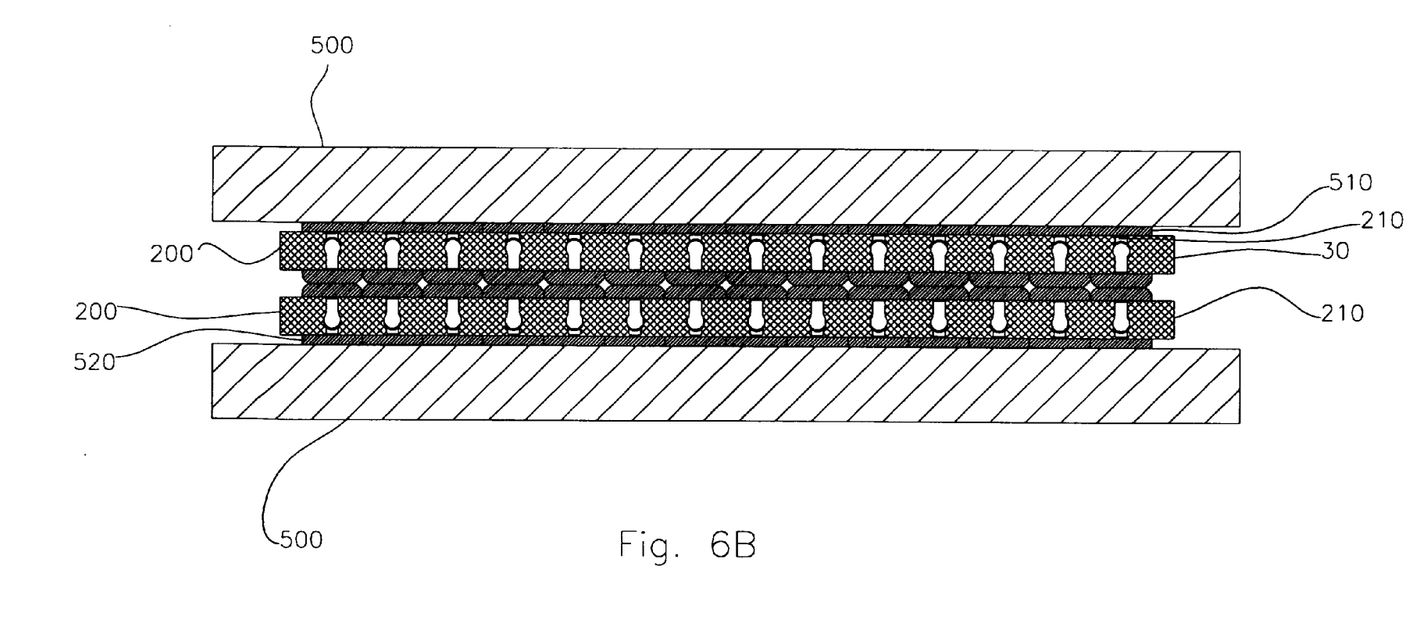
FIG. 6b depicts a schematic front view of two bondable bracket braces positioned on a tooth surface according to one embodiment of the present invention.

In step 504, bondable bracket brace 200 is positioned on the tooth surface. Referring to FIGS. 6a and 6b, two bondable bracket braces 200 are shown, with one being attached to upper teeth 510, and one being attached to lower teeth 520. Gums 500 are shown for reference purposes. Cloth-like body 30 of bondable bracket brace 200 is now in its first state—it is malleable and flexible. This allows bondable bracket brace 200 to be easily positioned on the tooth surface. In one embodiment, bondable bracket braces 200 are positioned substantially in the center of the upper and lower tooth surfaces spaced from gums 500 and the biting surface of the teeth. The positioning, however, may be dependent on the condition of the patient, including, inter a the severity and location of the problem, the patient's age, etc. As is understood by one of ordinary skill in the art, bondable bracket braces 200 may be positioned anywhere on the surface of the teeth where they may be securely bonded and where they may be effectively secured together to stabilize the mandible and/or the maxilla.

Prior to positioning bondable bracket braces 200 on the tooth surfaces, adhesive may be applied to the tooth surfaces. In one embodiment, a primary adhesive layer 530 is applied to the prepared tooth surface. Preferably, a light-curable epoxy is used; however, other types of adhesives may be used. Examples of suitable epoxies include Loctite #3321 and Loctite #3311 adhesives, both manufactured by Loctite Corporation, headquartered in Rocky Hill, Conn. Other standard dental adhesives, such as Fuji Ortho™, manufactured by G. C. America Inc., Chicago, Ill., or 3M™ Vitremer™ Tri-Cure Glass Ionomer, manufactured by 3M Corporation, St. Paul, Minn., may be used. In another embodiment, if bondable bracket brace 200 is pre-impregnated with an adhesive, it may not be necessary to apply adhesive to the tooth surface.

According to another embodiment, fiber straps may also be used in the initial positioning of bondable bracket brace 200. Fiber straps may be wrapped around the tooth surface to position and secure bondable bracket braces 200 to the tooth surfaces. Once in position, bondable bracket brace 200 is ready for wetting or, if pre-impregnated with epoxy, ready for curing.

As discussed with reference to FIG. 4, positioning of bondable bracket brace 200 may be accomplished with positioning bracket 400.

In step 506, adhesive is applied to the cloth-like body 30 of bondable bracket brace 200. To do this, the adhesive is wicked into the cloth-like body 30. This may include soaking cloth-like body in the adhesive until it is saturated. Preferably, the same type of adhesive applied to the tooth surface is wicked into the cloth-like body 30. This application forms secondary epoxy layer 540 on the back surface of cloth-like body 30.

If bondable bracket brace 200 is pre-impregnated with adhesive, it may not be necessary to apply additional adhesive to bondable bracket brace 200.

Once applied and wetted, cloth-like body 30 is contiguous with the tooth surface and is translucent enough to allow light to pass through and under cloth-like body 30. The small interdental spaces that are accessible to the light are also translucent. If the epoxy, or similar adhesive, is inhibited from interacting with the dentin by an inhibiting material, cloth-like body 30 will not adhere at that surface interface. For example, as explained above, cloth-like body 30 is provided with lift-off tabs that inhibit epoxy from contacting the surface of the teeth. As mentioned above, a suitable inhibiting material is Teflon®. Other suitable inhibiting materials may also be used. Because there is no adhesion between cloth like body 30 and the tooth surface at these points, the surface interface forms a point of removal, or a lift-off tab 540.

In step 508, once cloth-like body 30 is saturated with adhesive, and any lift-off tabs 340 are prepared, bondable bracket brace 200 is cured into position. The cure cycle is initiated by applying visible or ultraviolet light to bondable bracket brace 200, in accordance with the adhesive manufacturer's instructions. The light energy penetrates bondable bracket brace 200 and cures bondable bracket brace 200 in position.

Other forms of energy, such as electromagnetic energy, including electro-magnetic resonance, or other electromagnetic forces, may be used to cure the adhesive when applicable.

Once cured, cloth-like body 30 takes on its second state. In this second state, cloth-like body 30 has properties consistent with a rigid fiber reinforced medical grade Class VI plastic arch bar without (FIGS. 1a and 1b) or with (FIG. 1c) fiber straps.

Figure 6C:
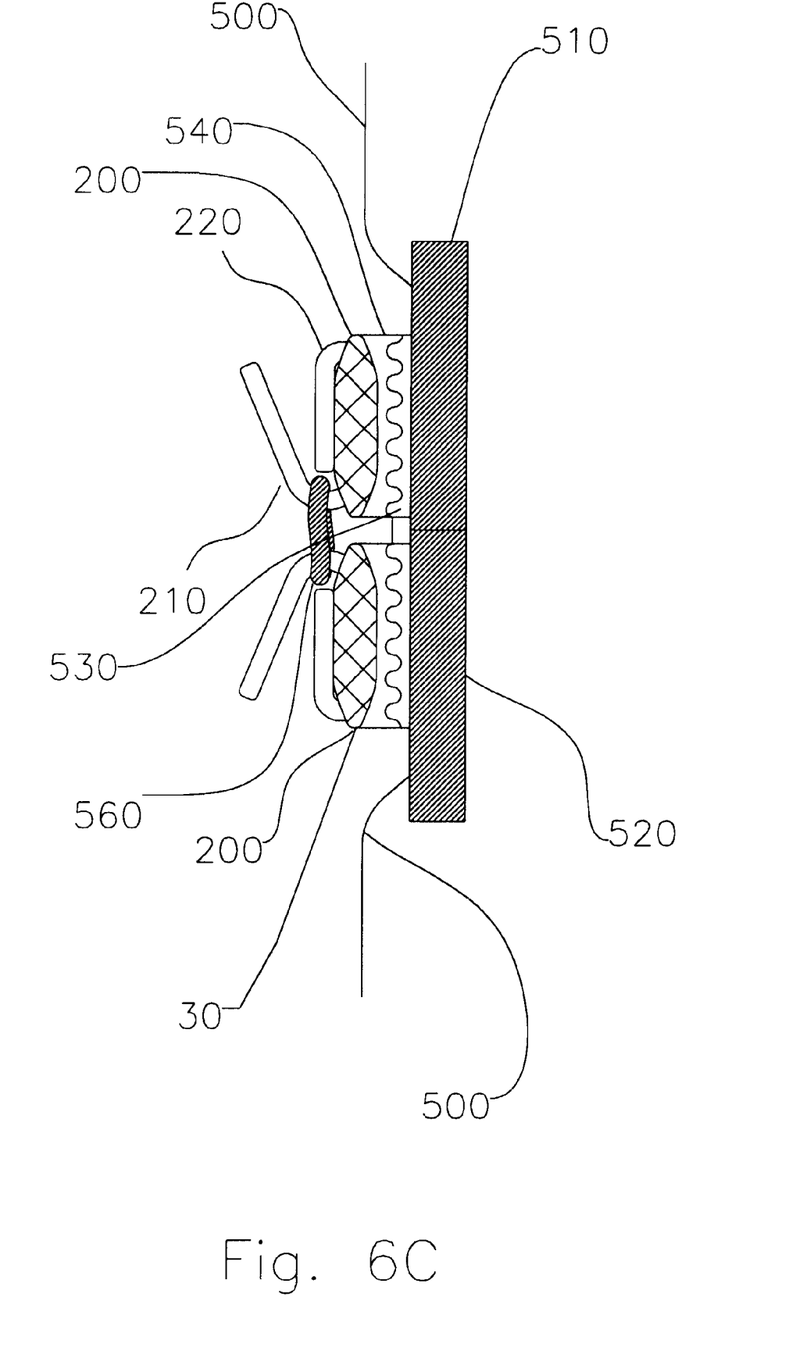
FIG. 6c depicts a schematic side view of two secured bondable bracket braces according to one embodiment of the present invention.
Figure 6D:
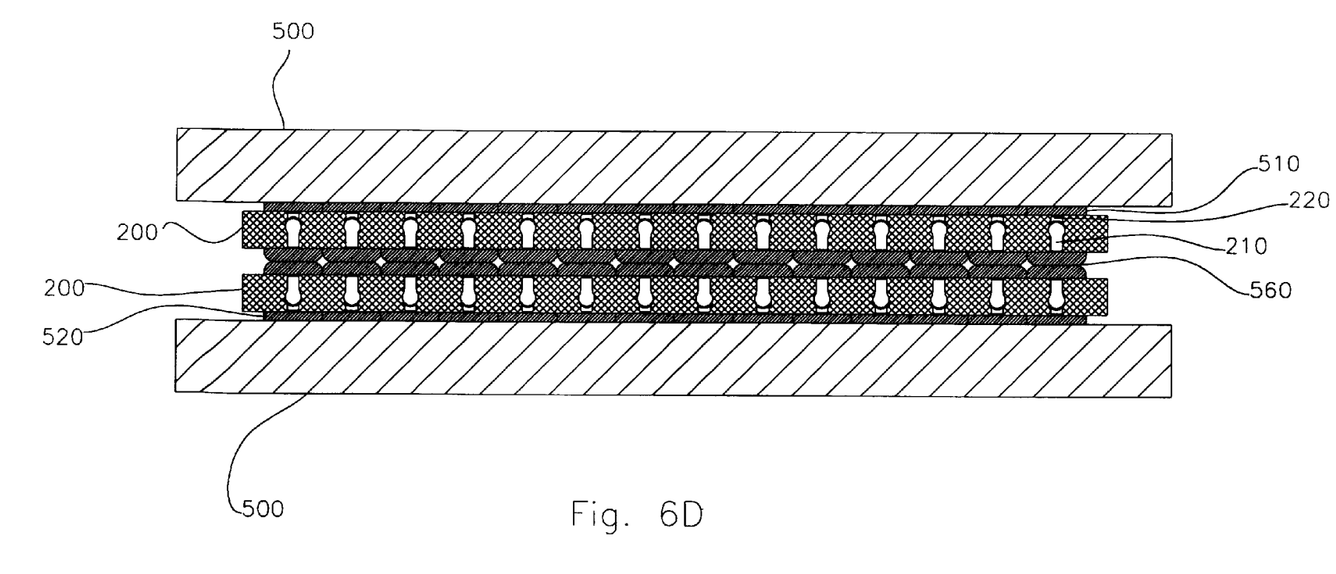
FIG. 6d depicts a schematic front view of two secured bondable bracket braces according to one embodiment of the present invention.
Figure 6E:
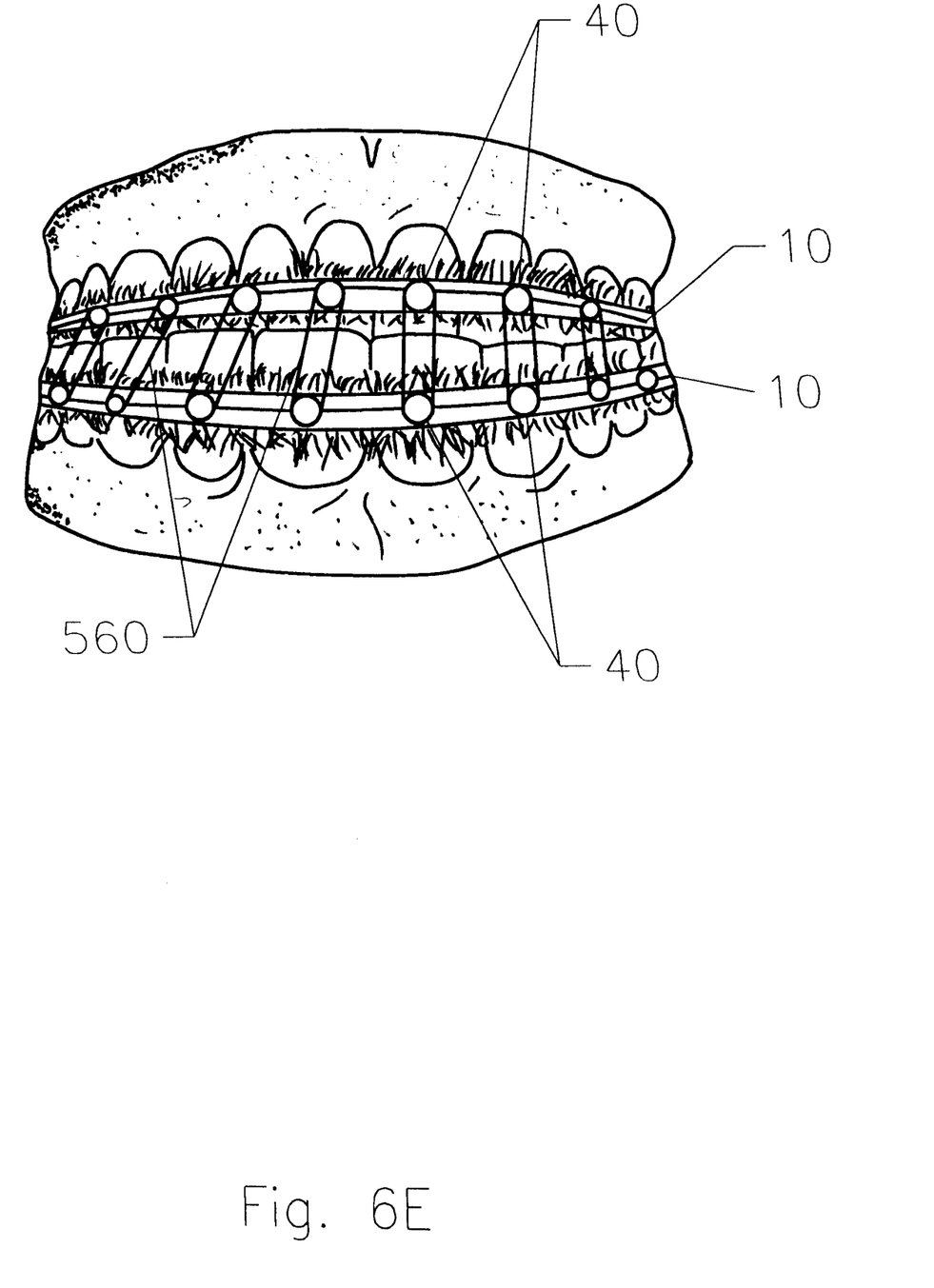
FIG. 6e shows a detail of the tooth surface having two secured bondable bracket braces according to one embodiment of the present invention.

In step 510, opposing or adjacent bondable bracket braces 200 may be secured to each other through attachment points 210. Attachment points 210 may be linked to one another by linking members 560. As discussed above, linking members 560 may be standard surgical wire, elastics, wire ties, fibers, or any other suitable linking member. Referring to FIGS. 6c and 6d, bondable bracket braces 200 are secured through linking members 360. Referring to FIG. 6e, a closed-mouth view of two secured bondable bracket braces 10 of FIGS. 1a–c is shown. Although this figure shows linking members 560 connecting attachment points 40 in a particular manner, other manners of connection may also be used.

In an alternate embodiment, one single bondable bracket brace may be used to secure both the upper and lower tooth surfaces which eliminates the use of linking members. This bondable bracket brace may be designed to permit breathing and the ingestion of food.

For large junctions, or where extra rigid holding is required, multiple bondable bracket braces may be placed over one another. Epoxy dams and templates may be fabricated to map the bonding area or fill large areas and voids.

The bondable bracket brace of the present invention may be removed by cutting fiber straps, if used, and peeling the bondable bracket brace off of the tooth surface via the lift-off tabs, with or without Teflon®.

As discussed earlier, the adhesive may adhere to bondable bracket brace 200 in such a manner that, upon removal, the adhesive and bondable bracket brace 200 separate from the tooth surface as one unit. This may be due to a stronger chemical bond between the adhesive and cloth-like body of bondable brace 10 than between the adhesive and the tooth surface. This results in less patient discomfort, less surgeon time, and an easier clean-up.

In addition to increasing the holding force of cloth-like bracket 30, fiber straps may replace standard interdental wires in conventional arch bars. Fiber straps may be passed into the interdental space, much like dental floss, and secured to a conventional arch bar. Securement to the conventional metal arch bar may be achieved via standard attachment mechanisms, knotting, epoxy, crimping, etc. The ultra-thin shapeable profile of fiber straps allow them to pass through gingival tissue with minimal force and trauma to maximize patient comfort. Further, antibiotics may be applied to the straps to decrease the chance of infection.

In general, the bondable bracket brace including cloth-like bracket and fiber straps according to the embodiments of the present invention provides a number of benefits. The use of ultra-thin fiber straps minimizes disturbance to the fracture site. The bondable bracket brace completely immobilizes the interface between the upper and lower teeth. The inclusion of lift-off tabs facilitates removal. The bondable bracket brace according to the embodiments of the present invention has bloodless application process, minimizes the need for sedation or anesthesia and eliminates the need for interdental wires. Further, because there is no blood, the risk of the transmission of diseases, such as hepatitis or HIV, are reduced or eliminated.

The cloth-like body of the bondable bracket brace disclosed herein has applications beyond the dental field. A bone immobilizing device having a cloth-like body may be used as a general splint or brace. For example, referring to FIG. 7, in step 700, an area for immobilization is prepared. This may include setting a fractured bone per standard bone setting procedures. Next, in step 702, a cloth-like body may be applied to the area that is to be immobilized. This may include wrapping the area to be immobilized with the cloth-like body. An intermediate layer may be applied to cover the skin surface so that the cloth-like body does not adhere to the skin.

Figure 7:
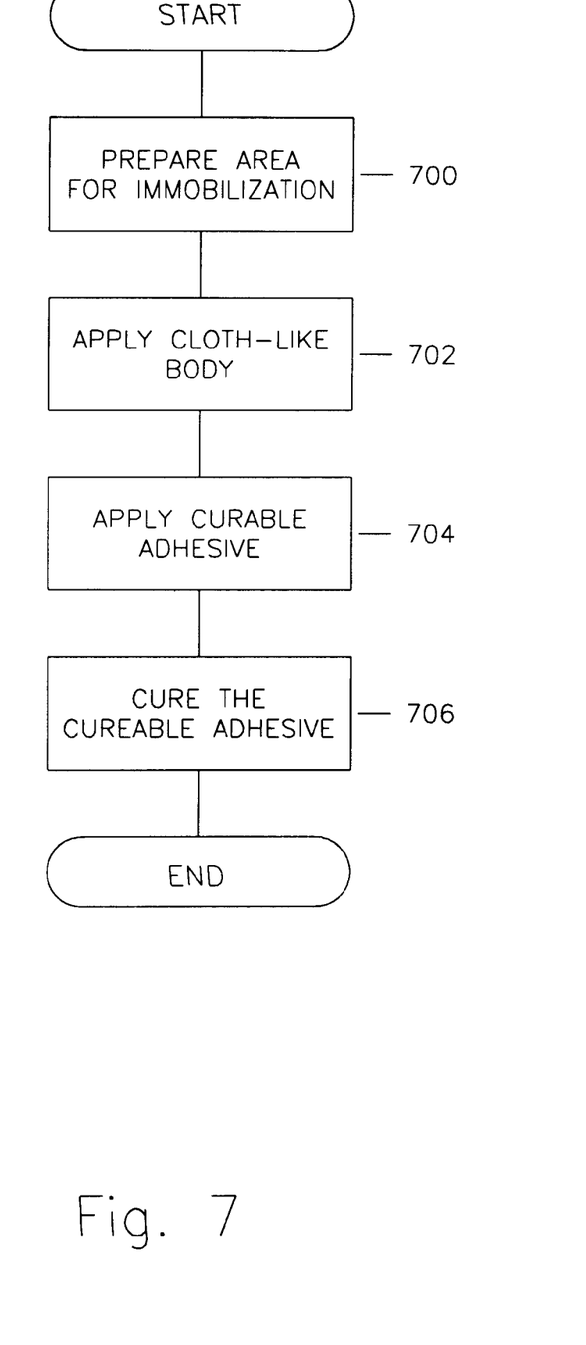
FIG. 7 depicts a flowchart of a method for bone immobilization according to one embodiment of the invention.

Next, in step 704, an adhesive, such as the light-curable adhesive discussed above, may be applied to the cloth-like body. In another embodiment, the cloth-like material may be pre-impregnated with an adhesive, so that once the pre-impregnated cloth-like body is positioned on the area to be immobilized, it is ready for curing. In step 706, once the cloth-like body has absorbed the curable adhesive, the adhesive is cured, resulting in a strong cast, brace, or splint.

The bone immobilizing device may have applications as a hand brace, a finger splint, above-and-below-the-knee cast or brace, arm casts, shoulder casts, neck braces, or any area where a cast or brace might be applied. The rapid curing and hardening of the bone immobilizing device eliminates patient discomfort and pain associated with the fracture and the setting of the fracture. Further, the bone immobilizing device allows on-the-spot medical treatment, allowing paramedics trained in bone setting to put the bone immobilizing device on an injured person quickly. The bone immobilizing device may be used in a temporary nature, such as for the transport of an injured person to a hospital, or it may be used in a more permanent nature, such as a conventional cast would.

The present invention overcomes disadvantages associated with the related art. The two-state, high-surface contact area, rapid-cure, bondable bracket brace, with or without fiber straps, includes an arch bar design that is aesthetically pleasing and allows for maximum patient comfort. The device improves surgeon safety, simplifies the application process, and dramatically improves holding forces over standard and direct bonding arch bars.

Although the present invention has been described in detail, it should be understood that various changes, substitutions, and alterations can be made without departing from the intended scope as defined by the appended claims.

What is claimed is:

1. An orthodontic appliance comprising:
   translucent base portion; and
   a plurality of attachment points on a first surface of said translucent base portion wherein a second surface of said translucent base portion is adapted to secure a plurality of teeth simultaneously.

2. The orthodontic appliance of claim 1, wherein said translucent base portion is selected from the group consisting of Kevlar®, nylon, fine metal mesh, and combinations thereof.

3. The orthodontic appliance of claim 1, further comprising at least one lift point for removing said orthodontic appliance.

4. The orthodontic appliance of claim 3, wherein said at least one lift point comprises a portion of non-stick material affixed to an edge of said translucent base portion.

5. The orthodontic appliance of claim 1, further comprising at least one fiber strap, wherein said at least one fiber strap is capable of securing said orthodontic appliance to a tooth surface.

6. The orthodontic appliance of claim 1, wherein said translucent base portion is pre-impregnated with an adhesive.

7. The orthodontic appliance of claim 1, wherein said attachment points protrude from a second surface of the translucent base portion.

8. The orthodontic appliance of claim 1, wherein said attachment points comprise pin and head structures.

9. The orthodontic appliance of claim 1, wherein said attachment points comprise hook structures.

10. The orthodontic appliance of claim 1 further comprising an adhesive layer, wherein said adhesive layer adheres to said orthodontic appliance such that said adhesive and said orthodontic appliance separate from a surface as one unit.

11. A bondable bracket brace comprising:
    a cloth-like body having a first surface for attachment to a tooth surface; and
    a plurality of attachment points on said cloth-like body;
    wherein said at least one lift point comprises a portion of non-stick material affixed to an edge of said cloth-like body.

12. A method of mandibular fixation comprising:
    preparing a surface of the teeth;
    applying a first adhesive layer to said prepared surface;
    positioning a bondable bracket brace on said first adhesive layer, said bondable bracket brace comprising a cloth-like body;
    creating at least one lift-off tab on said cloth-like body;
    curing said adhesive; and
    securing an object to said bondable bracket brace with a linking member.

13. The method of claim 12, wherein said step of creating said lift-off tab comprises:
    placing a non-stick material on said cloth-like body.

14. A method of maxillomandibular fixation comprising:
    securing a first orthodontic appliance on a first tooth surface connected to a maxilla, the first orthodontic appliance comprising a translucent base portion and a plurality of attachment points on the translucent base portion;
    securing a second orthodontic appliance on a second tooth surface connected to a mandible, the second orthodontic appliance comprising a translucent base portion and a plurality of attachment points on the translucent base portion; and
    securing the first orthodontic appliance to the second orthodontic appliance with at least one linking member, the linking member connecting at least one of the attachment points on the first orthodontic appliance with at least one of the attachment points on the second orthodontic appliance;
    wherein the first and second orthodontic appliances each secure a plurality of teeth simultaneously.

15. The method of claim 14, wherein said step of securing a first orthodontic appliance on a first tooth surface connected to a maxilla comprises:
    applying a first adhesive to the first tooth surface;

positioning the translucent base portion of the first orthodontic appliance on the adhesive; and curing the adhesive.

16. The method of claim 15, wherein said step of securing a first orthodontic appliance on a first tooth surface connected to a maxilla further comprises:

applying a second adhesive to the translucent base portion of the first orthodontic appliance.

17. The method of claim 15, wherein said the translucent base portion of the first orthodontic appliance is pre-impregnated with an adhesive.

18. The method of claim 15, wherein curing said adhesive comprises exposing said adhesive to visible light.

19. The method of claim 15, wherein curing said adhesive comprises exposing said adhesive to ultraviolet light.

20. The method of claim 15, wherein curing said adhesive comprises exposing said adhesive to electromagnetic energy.

21. The method of claim 14, wherein said step of securing a second orthodontic appliance on a second tooth surface connected to a mandible comprises:

applying a first adhesive to the second tooth surface;

positioning the translucent base portion of the second orthodontic appliance on the adhesive; and curing the adhesive.

22. The method of claim 21, wherein said step of securing a second orthodontic appliance on a second tooth surface connected to a mandible further comprises:

applying a second adhesive to the translucent base portion of the second orthodontic appliance.

23. The method of claim 21, wherein said the translucent base portion of the second orthodontic appliance is pre-impregnated with an adhesive.

24. The method of claim 21, wherein curing said adhesive comprises exposing said adhesive to visible light.

25. The method of claim 21, wherein curing said adhesive comprises exposing said adhesive to ultraviolet light.

26. The method of claim 21, wherein curing said adhesive comprises exposing said adhesive to electromagnetic energy.

27. The method of claim 14, further comprising:

securing a fiber strap from at least one of the first and second orthodontic appliances to a tooth.

28. The method of claim 14, further comprising creating at least one lift-off tab on the translucent base portion of at least one of the first and second orthodontic appliances.

29. The method of claim 28, wherein said step of creating said lift-off tab comprises:

placing a non-stick material on said translucent base portion.

* * * * *